United States Patent [19]

Fuchs et al.

[11] Patent Number: 4,782,174

[45] Date of Patent: Nov. 1, 1988

[54] PROCESS FOR THE PREPARATION OF CERTAIN PAIRS OF ENANTIOMERS OF α-CYANO-3-PHENOXY-4-FLUOROBENZYL PERMETHRATE

[75] Inventors: Rainer Fuchs; Andreas Wittig, both of Wuppertal, Fed. Rep. of Germany

[73] Assignee: Bayer Aktiengesellschaft, Leverkusen, Fed. Rep. of Germany

[21] Appl. No.: 874,989

[22] Filed: Jun. 16, 1986

[30] Foreign Application Priority Data

Jun. 25, 1985 [DE] Fed. Rep. of Germany ....... 3522629

[51] Int. Cl.[4] ......................................... C07C 121/75
[52] U.S. Cl. .................................................. 558/354
[58] Field of Search ......................................... 558/354

[56] References Cited

U.S. PATENT DOCUMENTS 4,133,826  1/1979  Warnant et al. .................... 558/407

FOREIGN PATENT DOCUMENTS 206149  12/1986  European Pat. Off. ............ 558/354

*Primary Examiner*—Anton H. Sutto
*Attorney, Agent, or Firm*—Sprung Horn Kramer & Woods

[57] ABSTRACT

A process for the preparation of a mixture principally comprising the
- (b) 1R-3R-αS+1S-3S-α and
- (d) 1R-3S-αS+1S-3R-αR enantiomers of the compound α-cyano-3-phenoxy-4-fluorobenzyl permethrate, comprising dissolving a mixture of all 8 stereoisomers of the compound α-cyano-3-phenoxy-4-fluorobenzyl permethrate in an alcohol having 2 to 4 carbon atoms, adding a secondary or tertiary alkyl amine having 2–6 carbon atoms in each alkyl moiety and allowing the mass to crystallize, whereby the desired mixture of enantiomers b) and d) crystallizes out of the solution.

5 Claims, No Drawings

PROCESS FOR THE PREPARATION OF CERTAIN PAIRS OF ENANTIOMERS OF α-CYANO-3-PHENOXY-4-FLUOROBENZYL PERMETHRATE

The present invention relates to a process for the preparation of certain pairs of enantiomers of α-cyano-3-phenoxy-4-fluorobenzyl permethrate, starting from the mixture of all the steric and optical isomers It is known that enantiomers of compounds having an acidic hydrogen atom on an asymmetric C atom can be epimerized by treatment with bases. The carbanions produced by the reaction with bases are continuously and rapidly transformed into their conceivable enantiomeric forms. This entails their briefly passing through the planar state (P. Sykes: Reaktionsaufklärung - Methoden und Kriterien der organischen Reaktionsmechanistik (Elucidation of reactions - methods and criteria of organic reaction mechanisms) Verlag Chemie 1973, page 133, and D. J. Cram: Fundamentals in Carbanion Chemistry, pages 85–105, Academic Press New York (1965).

This case is observed, for example, also in the easy base-catalyzed epimerization of optically active mandelonitrile of the formula

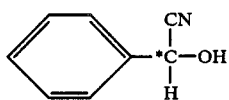

and of the corresponding methyl ether of the formula

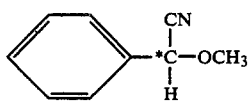

to give the racemic compounds. (Smith: J. Chem. Soc. 1935, page 194 and Smith: Ber. 64 (1931) page 427).

Depending on the solubility of the equilibrium partners of an epimerization equilibrium in the labile diastereomer, it is possible for the equilibrium to be displaced very greatly or completely to one side when a part crystallizes out. This case is designated "second order asymmetric transformation" (K. Mislow, Introduction to Stereochemistry, W. C. Benjamin Inc. New York, Amsterdam 1966, page 122 at the top).

However, practical application of this effect is possible only if a solvent can be found in which one stereoisomer and/or its mirror image is more readily soluble and the other stereoisomer and/or its mirror image is more sparingly soluble.

A reaction of this type has, for example, already been disclosed for the optically active -cyano-(RS)-3-phenoxybenzyl 2,2-dimethyl-3R-(2,2-dichlorovinyl)-cyclopropane-1R-carboxylate (DE-OS (German published specification) No. 2,718,039). Ammonia and amines are used as epimerizing bases. Acetonitrile and lower alkanols are used as solvents. However, this entails starting from the ester of a particular enantiomer of the carboxylic acid (1R3R).

There is no indication whatever that this process can also be used to achieve a separation of certain stereoisomers, by epimerization of the others, from the racemic mixture of all 8 stereoisomers of the abovementioned compound.

Furthermore, it is disclosed in DE-OS (German published specification) No. 2,903,057 that the 4 stereoisomeric α-cyano-αR,S)-3-phenoxybenzyl esters of a racemic carboxylic acid can be epimerized, by treatment with bases, at the α-carbon atom next to the cyano group, and a single pair of enantiomers can be crystallized out of suitable solvents. In this case too the solvents mentioned as suitable are lower alcohols, in particular methanol. The base used is aqueous ammonia.

According to EP-OS (European published specification) No. 22,382, a process for the conversion of the stereoisomeric mixture of the 4 cis-isomers of α-cyano-3-phenoxy-5-benzyl permethrate into a pure pair of enantiomers by crystallization of the more sparingly soluble pair of enantiomers from a suitable solvent takes place similarly, by subsequent epimerization with a base of the other pair of enantiomers remaining in solution, and renewed crystallization out of the more sparingly soluble pair of enantiomers. These crystallizations and epimerizations are carried out in separate steps. The solvents disclosed as being suitable for this are hydrocarbons, in particular hexane. The bases used are amines, in particular triethylamine.

DE-OS (German published specification) No. 3,115,881 discloses another process for the conversion of the stereoisomeric mixture of all 4 cis-isomers of α-cyano-3-phenoxybenzylα3-(2,2-dichlorovinyl)-2,2-dimethylcyclopropanecarboxylate into a single pair of enantiomers. This entails an organic amine being used simultaneously as the solvent and as the base. Triethylamine and diisopropylamine are described as being very suitable for this purpose. Tri-n-propylamine and n-butylmethylamine are mentioned as being unsuitable. However, this process also operates with a sterically homogeneous racemic acid part (cis-isomers). In this case too there is no indication whatever of whether a separation of individual stereoisomers from the mixture of all 8 conceivable stereoisomers is also possible.

It is impossible to make any predictions about which solvents will be suitable for the separation of enantiomers or diastereomers of the pairs of enantiomers Thus, it is necessary to develop a suitable separating system for each individual compound, and with cis-trans isomers also for each individual cis and/or trans pair of stereoisomers. Experience with cases where the situation is, in principle, similar can only occasionally be extrapolated, and then in an unpredictable manner.

In particular, it is not evident from the cited literature whether, and with which solvents, it is possible simultaneously to separate out the desired cis- and trans-diastereomers.

α-Cyano-3'-phenoxy-4'-fluorobenzyl 2,2-dimethyl-3-dichlorovinylcyclopropanecarboxylate(permethrate) has the structural formula I

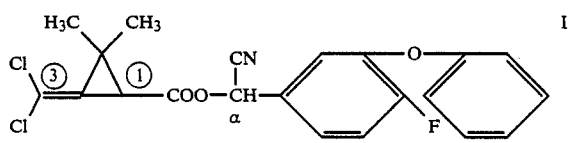

The compound has three centers of asymmetry ①, ③ and α. Thus, it exists in the following pairs of enantiomers:

| a: | 1R-3R-αR + 1S-3S-αS | 1,3 cis |
|---|---|---|

| | -continued | |
|---|---|---|
| b: | 1R-3R-αS + 1S-3S-αR | |
| c: | 1R-3S-αR + 1S-3R-αS | } 1,3 trans |
| d: | 1R-3S-αS + 1S-3R-αR | |

The pairs of enantiomers b and d are particularly active against numerous pests of economic interest.

In the industrial preparation of the compound of the formula I the ratios of the pairs of enantiomers a–d can be varied only within a certain narrow range. For example, in a typical compound of the formula I prepared industrially, the pairs of enantiomers a–d are present in the following ratio (relative to 100%)

a=24.5% b=17.5% c=34.5% d=23.5%.

The intention was to find a process by which the ratio of the pairs of enantiomers a–d in the mixture of all enantiomers is changed in favor of the pairs of enantiomers b and d.

It has been found that a mixture of all 8 stereoisomers of the compound α-cyano-3-phenoxy-4-fluorobenzyl permethrate can be converted into the pairs of enantiomers (b) 1R-3R-αS+1S-3S-α-R and (d) 1R-3S-αS+1S-3R-αR by dissolving this mixture of all the stereoisomers in an alkanol having 2–4 C atoms, adding as base a secondary or tertiary amine having, in each case, 2–6 C atoms in each alkyl moiety, and crystallizing the mixture of the pairs of enantiomers b and d from the resulting solution, the ratio of the pairs of enantiomers b/d which crystallize out together corresponding to the cis/trans ratio of the pairs of enantiomers (a+b)/(c+d) used.

It was surprising that it was unnecessary for this process to start from an ester which was sterically homogeneous in the acid part, but that it was possible to convert the mixture of all 8 stereoisomers of the cis- and trans-series, which is obtained industrially, into a mixture now consisting essentially only of 4 cis- and trans-stereoisomers.

The process according to the invention is carried out in an alkanol having 2–4 C atoms as the solvent. Isopropanol is preferably used.

Secondary or tertiary alkylamines having, in each case, 2–6 C atoms in each alkyl moiety are used as the base. Di-iso-butylamine and tri-n-butylamine are preferably used.

The ratio of mixing between alkanol and amine (in parts by weight) can vary in a range of alkanol/amine= 1,000/1 to 1/10. A ratio of mixing of alkanol/amine of 100/0.5 to 100/20 is preferred.

The ratio of mixing of the industrial product of the structural formula I which is used with the alkanol which is used (in parts by weight) can vary in a range from I/alkanol=10/1 to 1/10. A range from 3/1 to ⅓ is preferred.

The alkanols and amines used are essentially anhydrous. The industrial cis/trans starting material is dissolved in the mixture of alkanol and amine base at 40°–80° C., preferably between 50° and 70° C. The solution is then cooled to −25° to +30° C. The crystallization can be accelerated by addition of a few microcrystals of the pairs of enantiomers b+d. However, the crystallization also takes place spontaneously. The pairs of enantiomers b+d are isolated in a customary manner, for example, by filtration or centrifugation.

The examples which follow illustrate the invention without indicating a restriction on its extent.

An industrial product of the following composition was used for the examples:

| Isomeric composition | Ia = 25.2% |
|---|---|
| (based on 100%) | Ib = 19.2% |
| | Ic = 32.2% |
| | Id = 23.3% |
| Content of active compound = 92% | |
| (Ia + b + c + d) | |

EXAMPLE 1

100 g of an industrial cis/trans mixture of all 8 stereoisomers of α-cyano-3-phenoxy-4-fluorobenzyl 3-(2,2-dichlorovinyl)-2,2-dimethylcyclopropanecarboxylate are dissolved in 100 g of isopropanol, heating to 50° C. After this mixture has been cooled to 20° C., 4 g of diisobutylamine are added. The mixture is then stirred at 20°–23° C. During this, spontaneous crystallization usually starts, and this can be accelerated by addition of a few seed crystals of Ib and Id. After the reaction mixture has been stirred at 20°–23° C. for 9 days, it is cooled to 5° C., and the resulting crystals are filtered off with suction. The crystals are washed 2 x with 50 ml of ice-cold isopropanol each time, sucked dry, and dried in air.

82.2 g (87.8% of theory) of a color crystalline product are obtained, which have a melting point of 82°–89° C. and the following isomer composition determined by HPLC (based on 100%):

Ia=0.8%, Ib=38.8%, Ic=1.9%, Id=58.5%.

EXAMPLE 2

100 g of the industrial cis/trans mixture of all 8 stereoisomers of α-cyano-3-phenoxy-4-fluorobenzyl 3-(2,2-dichlorovinyl)-2,2-dimethylcyclopropanecarboxylate are reacted as described in Example 1 with the alkanols and amines listed in Table 1. The results are compiled in Table 1.

TABLE 1

| Alkanol + Amine | Amount in g | Stirring time in days | Yield of crystalline product, % of theory | Isomer composition | | | |
|---|---|---|---|---|---|---|---|
| | | | | Ia | Ib | Ic | Id |
| Methanol | 100 | 9 | 0 | — | — | — | — |
| Diisobutylamine | 4 | | decomposition occurs | | | | |
| n-Propanol | 100 | 9 | 64 | 0.5 | 31.8 | 1.9 | 65.8 |
| Diisobutylamine | 4 | | | | | | |
| n-Butanol | 100 | 9 | 51.3 | 0.4 | 16.1 | 2.2 | 81.0 |
| Diisobutylamine | 4 | | | | | | |
| sec.-Butanol | 100 | 9 | 49 | — | — | — | — |

TABLE 1-continued

| Alkanol + Amine | Amount in g | Stirring time in days | Yield of crystalline product, % of theory | Isomer composition Ia | Ib | Ic | Id |
|---|---|---|---|---|---|---|---|
| Diisobutylamine | 4 | | | | | | |
| tert.-Butanol | 100 | 9 | 40 | — | — | — | — |
| Diisobutylamine | 4 | | | | | | |
| Ethanol | 100 | 7 | 55 | 0.24 | 15.8 | 1.4 | 82.6 |
| Diisobutylamine | 4 | | | | | | |

It will be understood that the specification and examples are illustrative but not limitative of the present invention and that other embodiments within the spirit and scope of the invention will suggest themselves to those skilled in the art.

What Is claimed:

1. A process for the preparation of a mixture principally comprising the
   (b) 1R-3R-αS+1S-3S-αR and
   (d) 1R-3S-αS+1S-3R-αR
enantiomers of the compound α-cyano-3-phenoxy-4-fluorobenzyl permethrate, comprising dissolving a mixture of all 8 stereoisomers of the compound α-cyano-3-phenoxy-4-fluorobenzyl permethrate in an alcohol having 2 to 4 carbon atoms, adding a secondary or tertiary alkyl amine having 2-6 carbon atoms in each alkyl moiety and allowing the mass to crystallize, whereby the desired mixture of enantiomers (b) and (d) crystallizes out of the solution.

2. A process according to claim 1, wherein the alkyl amine is at least one of di-iso-butylamine and tri-n-butylamine.

3. A process according to claim 1, wherein the alcohol is isopropanol.

4. A process according to claim 1, wherein the weight ratio of alcohol/amine is from 1,000/1 to 1/10.

5. A process according to claim 1, wherein the weight ratio of alcohol/amine is from 100/0.5 to 100/20.

* * * * *